US00PP33733P2

(12) United States Plant Patent
Uebelhart

(10) Patent No.: US PP33,733 P2
(45) Date of Patent: Dec. 7, 2021

(54) ***HELIOPSIS* PLANT NAMED 'FIRE TWISTER'**

(50) Latin Name: *Heliopsis helianthoides*
Varietal Denomination: Fire Twister

(71) Applicant: Georg Uebelhart, Salzhausen (DE)

(72) Inventor: Georg Uebelhart, Salzhausen (DE)

(73) Assignee: JELITTO STAUDENSAMEN GMBH, Schwarmstedt (DE)

( * ) Notice: Subject to any disclaimer, the term of this patent is extended or adjusted under 35 U.S.C. 154(b) by 0 days.

(21) Appl. No.: 17/239,495

(22) Filed: Apr. 23, 2021

(51) Int. Cl.
*A01H 5/02* (2018.01)
*A01H 6/14* (2018.01)

(52) U.S. Cl.
USPC ..... Plt./437
CPC ..... *A01H 6/14* (2018.05)

(58) Field of Classification Search
USPC ..... Plt./437
CPC ..... A01H 6/14; A01H 5/02
See application file for complete search history.

*Primary Examiner* — Keith O. Robinson
(74) *Attorney, Agent, or Firm* — Penny J. Aguirre

(57) ABSTRACT

A new cultivar of *Heliopsis* plant named 'Fire Twister' that is characterized by its short plant height (70 to 100 cm) depending on soil conditions, its stems that are sturdy and grey-purple to brown in color, its very dark green color foliage that is tinged black on the upper surface and slightly fading towards the end of the season, its medium sized inflorescences that open orange-red to grey-purple in color with a disc reddish in color and fading to orange, orange-red and grey-orange, its inflorescences with two, occasionally three whorls of ray florets.

2 Drawing Sheets

Botanical classification: *Heliopsis helianthoides* var. *scabra*.

Variety denomination: 'Fire Twister'.

CROSS REFERENCE TO A RELATED APPLICATION

This application is related to a European plant breeders' rights application filed on Dec. 11, 2018, application No. 2018/3281. There have been no offers for sale anywhere in the world prior to the effective filing date of this Application and no accessibility to one of ordinary skill in the art could have been derived from the printed plant breeder's rights documents. This application is co-pending with a U.S. Plant Patent Application filed for a plant derived from the same breeding program that is entitled *Heliopsis* Plant Named 'Funky Spinner' (U.S. Plant patent application Ser. No. 17/239,506).

BACKGROUND OF THE INVENTION

The present invention relates to a new and distinct cultivar of *Heliopsis* plant, botanically known as *Heliopsis helianthoides* var. *scabra* 'Fire Twister' and will be referred to hereinafter by its cultivar name, 'Fire Twister'.

'Fire Twister' was derived from a controlled breeding program conducted by the Inventor in a nursery in Schwarmstedt, Germany. The breeding program focuses on obtaining new cultivars of *Heliopsis* with a sturdy, short plant habit, dark purple foliage and stems, red to bronze flowers with more than one whorl of ray florets. 'Fire Twister' was selected in summer of 2013 by the Inventor as a single unique plant derived from a cross made in 2012 between unnamed and unpatented proprietary plants from his breeding program; identified as sowing no. H10006.

Asexual propagation of the new cultivar was first accomplished using tissue culture using meristematic tissue under the direction of the Inventor in summer of 2015 in Rijswijk, The Netherlands. Asexual propagation by stem cuttings, division and tissue culture has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Fire Twister' as a unique cultivar of *Heliopsis*.

1. 'Fire Twister' exhibits a short plant height (70 to 100 cm) depending on soil conditions.
2. 'Fire Twister' exhibits stems that are sturdy and grey-purple to brown in color.
3. 'Fire Twister' exhibits very dark green color foliage that is tinged black on the upper surface and slightly fading towards the end of the season.
4. 'Fire Twister' exhibits medium sized inflorescences that open orange-red to grey-purple in color with a disc reddish in color and fading to orange, orange-red and grey-orange.
5. 'Fire Twister' exhibits inflorescences with two, occasionally three whorls of ray florets.

The female and male parent plants of 'Fire Twister' both differ from 'Fire Twister' in having a taller plant height, a floppy plant habit, small to medium sized inflorescences with less ray florets per inflorescence, and yellow-red to bicolor ray florets. 'Fire Twister' can also be compared to *Heliopsis* cultivars 'Bleeding Hearts' (not patented), 'Summer Nights' (not patented) and 'Funky Spinner'. 'Bleeding Hearts' is similar to 'Fire Twister' in inflorescence size, ray floret coloration, stems that are dark in color, and foliage that is purple in color. 'Bleeding Hearts' differs from 'Fire Twister' in having a much taller plant height, inflorescences with a single whorl of ray florets, and variability in habit, flower size and flower color due to being a seed strain. 'Summer Nights' is similar to 'Fire Twister' in having stems that are purple in color, inflorescences with a similar disc color, and a similar flowering time. 'Summer Nights ' differs from 'Fire Twister' in having a much taller plant height, a floppy plant habit, foliage that turns green in the summer, ray florets that are yellow with a red base, and variability in habit, flower size and flower color due to being a seed strain. 'Funky Spinner' differs from 'Fire Twister' in having inflorescences with ray florets that are yellow-orange in color with the lower ⅓$^{rd}$ of the ray florets orange-red to grey-purple in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales prior to the filing date but less than one year prior to the effective filing date. Disclosures include but may not be limited to Breck's, Prides Corner, Missouri Botanical Gardens, Heritage Perennials, Sugar Creek Gardens, Dutch Bulbs, Creek Hill Gardens, Pioneer Gardens, Perennials Plus, Milaegers, Thanyathip Rice Compnay, Uncontained Life, Green Leaf Plants, Vitro Westland, All Plant Young Plants, Siebenthaler's, Le Jardin d' Adoué, Perennial Nursery de Hessenhof, Stauden Stade, Fleury Horticulture, Tuingoed Foltz, Northshore plant Club, Greenity34, Marcel de Wagt, Tuinadvies, De Border, Le Jarden Du Moran, De Werkplaats, Schachtschneider, Podvorye, Lichhtnelke, e Flora, Alwerts Gardens, Les Vivaces de Sandrine et Thierry, Hogendoorn, Hortensia, Gartnerei Kohlor, Majland Stauder, Bill Moore & Company, Aris Keepsake Plants, Acer Gardens, Caggbrokcob, Sadfloxo, The Herb Factory, and Balzes.

BRIEF DESCRIPTION OF THE DRAWINGS

The accompanying color photographs illustrate the overall appearance and distinct characteristics of the new *Heliopsis*. The photographs were taken of a plant 7 months in age as field grown in Noordwijkerhout, The Netherlands.

The photograph in FIG. 1 provides a side view of a plant of 'Fire Twister' in bloom.

Figure 1:
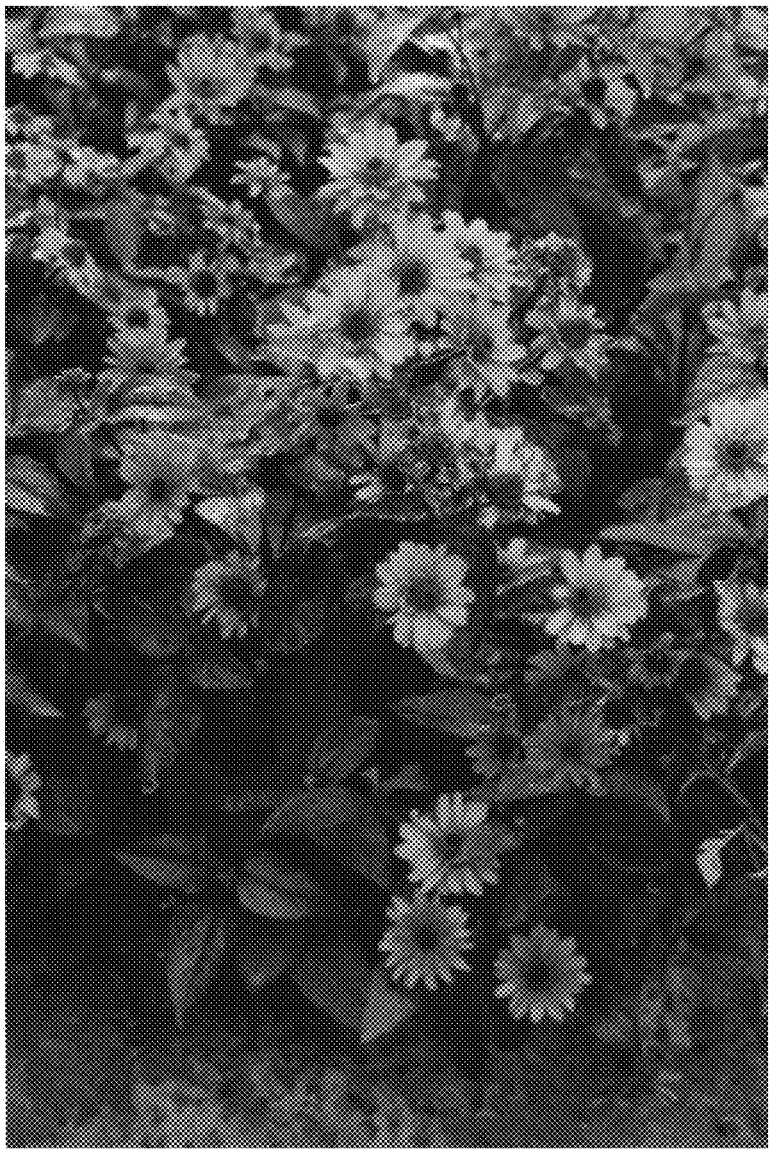
Figure 2:
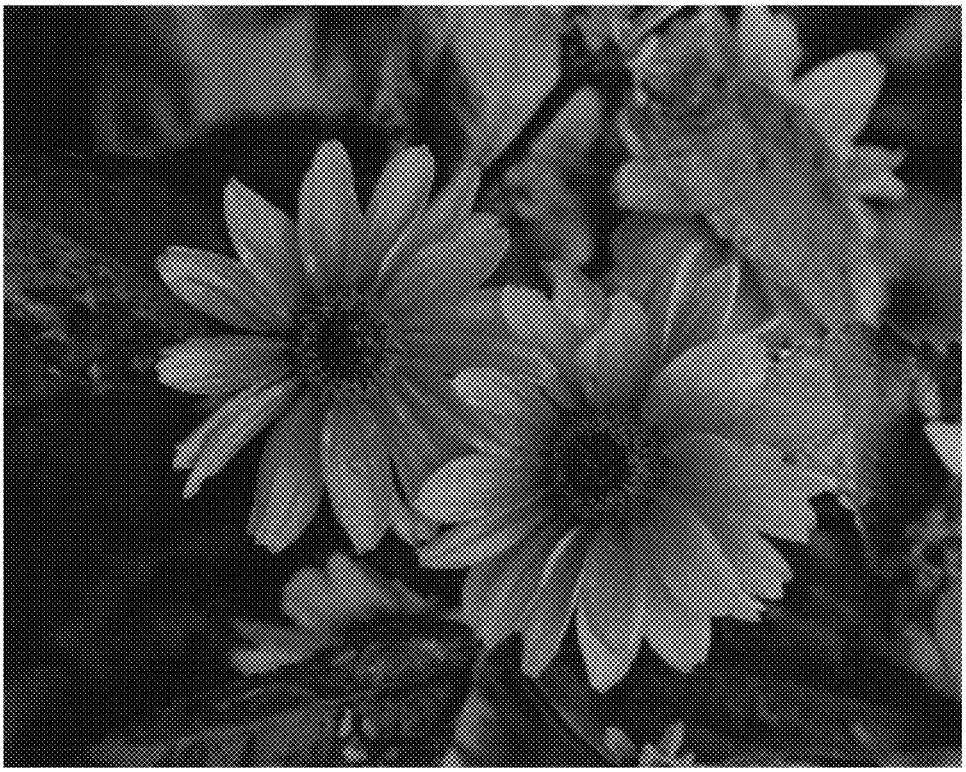

The photograph in FIG. 2 provides a close-up view of the inflorescences of 'Fire Twister'.

Figure 3:
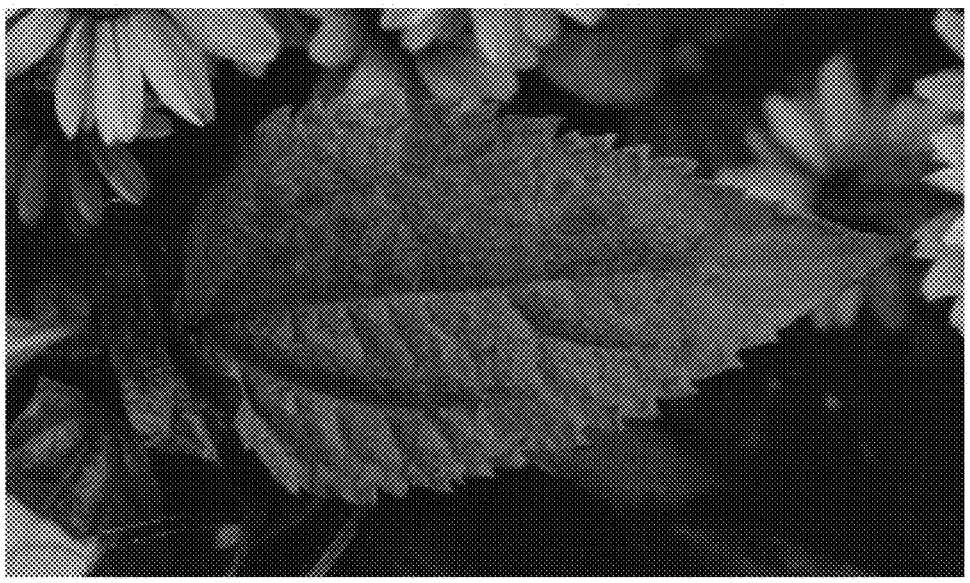

The photograph in FIG. 3 provides a close-up view of a leaf of 'Fire Twister'.

The colors in the photographs are as close as possible with the photographic and printing technology utilized and the color values cited in the detailed botanical description accurately describe the colors of the new *Heliopsis*.

DETAILED BOTANICAL DESCRIPTION

The following is a detailed description of plants 7 months in age as field grown in Noordwijkerhout, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming season.*—8 weeks from late summer into autumn in The Netherlands.

*Plant type.*—Herbaceous perennial.

*Plant habit.*—Broadly spreading and upright.

*Height and spread.*—Average of 65 cm in height (soil level to top of foliar plane), 70 cm in height (soil level to top of floral plane), and 90 cm in spread as a 7-month old plant, reaches 70 to 100 cm in height and an average of 90 cm in spread in the landscape depending on soil conditions.

*Hardiness.*—At least in U.S.D.A. Zones 4 to 9.

*Diseases and pests.*—No susceptibility or resistance to diseases or pests has been observed.

*Root description.*—Fibrous.

*Propagation.*—Stem cuttings, tissue culture and division.

*Root development.*—1 to 2 weeks for root initiation, a fully rooted young plant is produced in three to four weeks.

*Growth rate.*—Moderate to highly vigorous.

Stem description:

*Stem shape.*—Slightly angled, 5-sided.

*Stem aspect.*—Main branches 50° from vertical, secondary branches 25° to main stem.

*Stem strength.*—Moderately strong.

*Stem color.*—Young stems; 146C, strongly tinged with colors between N186C and 200B, mature stems; between N186C and 200A.

*Stem surface.*—Young stems moderately to densely pubescent, hairs 0.5 mm in length, 156D in color, moderately glossy.

*Branch size.*—Average of 17.6 cm in length, 4 mm in diameter.

*Internode length.*—Average of 8.2 cm.

*Branching.*—Freely branching, average of 8 main branches, 4 lateral branches per main branch.

Foliage description:

*Leaf division.*—Simple.

*Leaf shape.*—Ovate to broadly lanceolate.

*Leaf base.*—Short, attenuate.

*Leaf apex.*—Acute.

*Leaf margin.*—Serrate.

*Leaf venation.*—Pinnate, upper surface 165A, lower surface 146A.

*Leaf attachment.*—Petiolate.

*Leaf arrangement.*—Opposite.

*Leaf surface.*—Upper surface; slightly rugose, very slightly glossy, lower surface; matte, moderately rugose, both surfaces moderately covered with very short strigose hairs, average of 0.3 mm in length, 156D in color.

*Leaf color.*—Young foliage upper surface; 143A, young foliage lower surface between 144B and 146C, mature upper surface; NN137A, top tinged 203B, mature lower surface; between 146B and 147B.

*Leaf size*.—Average of 11.2 cm in length and 6.4 cm in width.

*Petiole*.—Strong, an average of 2.2 cm in length and 3 mm in diameter, upper surface; slightly glossy, between N199A and N199B in color, slightly covered with very short strigose hairs, 0.3 mm in length, too small to measure color, lower surface; matte, 145A in color, glabrous.

Flower description:

*Inflorescence type*.—Rotate, terminal capitulum consisting of a receptacle, disc florets and ray florets.

*Lastingness of inflorescence*.—Average of 10 days, persistent.

*Fragrance*.—Faint and sweet.

*Quantity of inflorescences*.—1 per lateral stem, 160 inflorescences and buds per plant.

*Inflorescence buds*.—About 1.7 cm in depth and 1.8 cm in diameter, broad oblong in shape, immature ray florets pointing upward (near vertical), a blend of 200C to 200D, immature involucral bracts 138B and tinged 200D in color.

*Inflorescence size*.—An average of 2 cm in depth and 6 cm in diameter.

*Receptacle*.—Triangular, average of 6 mm in depth and 5 mm in diameter, disc diameter 1.7 cm, 157B in color.

*Peduncle*.—Round with axial ribs, 9.6 cm in length, 2.5 mm in diameter, strong, upright, straight on top of lateral branch, between N186C and 200B, slightly glossy, densely covered with very short adpressed hairs, an average of 0.5 mm in length, 156D in color.

*Involucral bracts* (*phyllaries*).—Rotate, oblong in shape, 16 per inflorescence, arranged in 2 rows, obtuse apex, broadly cuneate base, margin entire, upper surface color 145D, striped 144B, lower surface color 137B, base 147A, average of 1 cm in length, 3 mm in width, surfaces matte and covered with pubescence; 0.3 mm in length, too small to measure color.

*Spine*.—Single bract present next to each individual disc floret, spirally placed on disc, one bract next to each individual disc floret, surface smooth, glabrous, and moderately glossy, 6 mm in length, 1 mm in diameter, oblanceolate in shape, obtuse apex, cuneate base, color; apex between 187A and 200B, mid-section and base 157D.

Ray florets (carpellate):

*Number*.—Average of 17, 2 rows.

*Arrangement*.—Rotate.

*Appearance*.—Moderately carinate, nearly horizontal.

*Shape*.—Elliptic to broadly oblanceolate.

*Aspect*.—Nearly horizontal.

*Size*.—Average of 3 cm in length and 1.1 cm in width.

*Petal apex*.—Not deeply praemorse.

*Petal base*.—Attenuate.

*Petal margins*.—Entire.

*Petal texture*.—Upper surface velvety and matte, lower surface moderately velvety and very slightly glossy.

*Petal color*.—When opening upper surface; between N34A and 183A to 183B, when opening lower surface; 175A to 175B, when fully open upper surface; N34A, changing at the tips ranging between N25B to N25C and N163C, fading to 17A, when fully open lower surface; N163C, veins 166B, fading to 21B to 21C with a central band of 151B to 151C.

Disc florets (perfect):

*Quantity*.—Average of 160.

*Shape*.—Tubular.

*Arrangement*.—Spirally placed on disc in 6 rows.

*Petal apex*.—Upper 12.5% free, acute, entire margins.

*Petal base*.—Lower 87.5% fused,

*Petal texture*.—Both surfaces glabrous, slightly glossy, non-rugose.

*Size*.—Average of 9 mm in length and 4 mm in width.

*Color*.—When opening upper and lower surface N34A and 178A, mid-section and base 151D, when fully open upper and lower surface 30B, mid-section and base 20A to 20B.

Reproductive organs:

*Presence*.—Disc flowers are perfect, ray flowers are carpellate.

*Gynoecium*.—Pistil; 1, per disc and ray floret, 1 cm in length, stigma; cleft, 3 mm in diameter, color between N186C and 200A, style; 8 mm in length, 164B in color, ovary; 157C to 157D in color.

*Androecium*.—Stamens; 5 per disc floret, filaments; 4 mm in length and 155A in color, anthers; narrow oblong in shape, 3 mm in length, 0.5 mm in width and 200A in color, pollen; moderate in quantity and 17A in color.

*Fruit and seed*.—No fruits or seeds observed to date.

It is claimed:

1. A new and distinct cultivar of *Heliopsis* plant named 'Fire Twister' as herein illustrated and described.

* * * * *